United States Patent

Bytyn et al.

[11] Patent Number: 5,874,737
[45] Date of Patent: Feb. 23, 1999

[54] GAS ANALYZER

[75] Inventors: Wilfried Bytyn, Stuttgart; Peter Seefeld, Bad Wimpfen; Stefan Vaihinger, Tübingen, all of Germany

[73] Assignee: Endress + Hauser Conducta Gesellschaft fur Mess- und Regeltechnik mbH + Co., Gerlingen, Germany

[21] Appl. No.: 812,571

[22] Filed: Mar. 6, 1997

[30] Foreign Application Priority Data

Mar. 6, 1996 [DE] Germany ............... 196 08 604.3

[51] Int. Cl.[6] .................................................. G01N 21/61
[52] U.S. Cl. ........................ 250/343; 250/338.5; 356/437
[58] Field of Search ............................. 250/338.5, 343; 356/437, 438, 439

[56] References Cited

U.S. PATENT DOCUMENTS

| | | | |
|---|---|---|---|
| 4,323,777 | 4/1982 | Baskins et al. | 250/338.5 |
| 4,709,150 | 11/1987 | Burough et al. | |
| 4,922,108 | 5/1990 | Modlinski et al. | 250/343 |
| 5,281,816 | 1/1994 | Jacobson et al. | 250/338.5 |
| 5,332,901 | 7/1994 | Eckles et al. | 356/437 |
| 5,341,214 | 8/1994 | Wong | 250/338.5 |
| 5,453,620 | 9/1995 | Wadsworth et al. | 250/343 |
| 5,559,333 | 9/1996 | Araya et al. | 250/343 |

FOREIGN PATENT DOCUMENTS

| | | |
|---|---|---|
| 2 166 382 | 4/1974 | Germany . |
| 3446756C1 | 10/1985 | Germany . |
| 4413670A1 | 3/1995 | Germany . |
| 94 20 231.1 | 3/1995 | Germany . |
| WO 94/17389 | 8/1994 | WIPO . |
| WO 96/01418 | 1/1996 | WIPO . |

OTHER PUBLICATIONS tm—Technisches Messen 60, 1993, Industrielle Gasanalyse, pp. 296–301.

*Primary Examiner*—Edward J. Glick
*Assistant Examiner*—Darren M. Jiron
*Attorney, Agent, or Firm*—Jones, Tullar & Cooper, P.C.

[57] ABSTRACT

A gas analyzer for continuously determining the concentration of a gas in a gas mixture, having a measuring cell, a radiation source, a detector and signal processing facilities, characterized in that the radiation source is slidingly arranged in the measuring cell.

20 Claims, 3 Drawing Sheets

GAS ANALYZER

BACKGROUND OF THE INVENTION

The present invention relates to a gas analyzer for continuously determining the concentration of a gas in a gas mixture, the analyzer consisting of an energy source, a measuring cell, a radiation source, a detector and signal-processing devices. The present invention relates furthermore to a measuring cell for the photometric measurement of a gas in a mixture of gases.

The analysis of gases by measuring devices operating on the principle of non-dispersive infra-red spectroscopy (NDIR) has long been known. It has a wide range of applications, including flue gas analysis, process metrology in the field of chemical process engineering, and also recently to an increasing extent the measuring and regulating of air and air quality in buildings.

The fundamental design for a gas analyzer is substantially the same in all cases. The radiation emitted by a radiation source passes through a measuring cell containing the gas to be measured and impinges on a detector. As the radiation travels through the cell, its initial intensity, as emitted by the source, is attenuated by absorption processes. The relationship between the gas concentration to be determined and the attenuation of the intensity is governed by the Lambert-Beer law. The generation of a detector signal with an adequate signal/noise ratio requires modulation of the radiation emitted by the radiation source. The gas to be measured enters the measuring cell either by diffusion or with the help of a pump.

Measuring devices of the above-mentioned type are known from U.S. Pat. No. 5,163,332 and GB Patent 1 398 97. The U.S. Pat. No. 5,163,332 describes an NDIR single beam gas analyzer having a measuring cell which can be operated in the diffusion mode. The cell consists of a closed tube having several discrete gas access openings distributed over the length of the tube. The gas exchange takes place via a membrane which covers the gas openings. The radiation source and the detector are mounted at both ends of the tubular measuring cell. The membrane system makes for a relatively complicated design of the measuring device. GB Patent 1 398 977 also describes a single-beam infra-red photometer for measuring gases, in which the lamp used as a radiation source is supplied with timing pulses by means of an oscillator. The radiation, which is thus modulated with a clock frequency of several Hz, travels along the gas-measuring path and passes through an optical filter, which is transparent to a certain wavelength, before arriving at a radiation-sensitive detector. The measuring cell consists of a tube, closed all round, having a reflecting inner surface. The radiation source and the detector are positioned at the respective ends of the tube. Gas is permitted to enter through a small opening near the optical filter or near the detector. The advantage of using a pulsed light source of this kind is that it permits small, lightweight, cheap, in principle battery-operated and portable but nevertheless efficient gas analyzers to be designed and built.

It is, however, disadvantageous that the known cells can only be used for a narrow measuring range, because the relationship between the concentration of the gas to be measured and the output signals is not linear and the measurement becomes inaccurate with increasing concentration.

SUMMARY OF THE INVENTION

It is an object of the present invention to refine the design of gas analyzers of the type referred to above in such a manner that the stated disadvantages are eliminated, and in particular the lengths of the cells can be optimally adapted to the respective gas concentration range to be measured.

This object is achieved by arranging the radiation source in the measuring cell in such a way that the source is movable.

With the gas analyzer according to the present invention it is a simple matter to adapt the absorption pathway between the radiation source and the detector to different concentration ranges of the gas to be measured, and thus to optimize the measurement accuracy in the concentration range to be monitored, corresponding to the logarithmic decrement in a range of 5–7 orders of magnitude.

This adaptation of the measuring range is of interest, for example, for measuring carbon dioxide ($CO_2$), because the $CO_2$ concentration ranges to be measured can be very different from case to case. In the area of air conditioning and ventilation engineering, it is necessary to monitor $CO_2$ concentrations between approx. 350 ppm (content of outdoor air) and 5000 ppm (MAK value [MAK=maximum allowable concentration at the workplace]). In the field of flue gas measurement, the $CO_2$ concentrations to be measured are typically between 10 and 20 vol.%. In special cases, $CO_2$ concentrations of up to 100 vol. % also need to be monitored (with less stringent resolution requirements).

When the radiation passes through the medium to be measured, the intensity of the radiation is attenuated by absorption processes. The relationships can be quantitatively described by the Lambert Beer law as follows: $\ln I/I_0 = -\epsilon c d$.

The ratio of radiation intensity I passing through the medium and the source intensity $I_0$ declines exponentially as a function of the concentration c and the length of the measuring path (length of the cell) c. The proportionality factor $\epsilon$ is the extinction coefficient.

Photometric measuring procedures possess an optimum operating point for extinction which is determined by the optical and electronic systems of the measuring device. It is already apparent from the aforementioned Lambert-Beer law that the relationship is not linear and that an ideal operating range exists for measuring extinction. The gas analyzer as claimed by the present invention now permits the layer thickness d, i.e., the distance between the radiation source and the detector, to be modified cheaply by mechanical means, even in the case of widely differing gas concentration ranges that require monitoring; and the extinction can at all times be maintained in the optimum operating range by means of this simple mechanical adjustment. The gas analyzer according to the present invention therefore permits the measuring accuracy to be specifically optimized for any desired concentration range.

The gas analyzer is advantageously so designed that the radiation source is movably mounted and can be fixed in position, e.g. by means of a clamping screw, in a longitudinal slot provided for this purpose in the measuring cell. It has proved particularly advantageous to arrange the radiation source in a holder, possibly provided with a reflector, and the holder is for its part fitted with a threaded hole for the clamping screw. In order to guarantee maximum possible variation of the layer thickness, the detector is mounted at one end of the measuring cell. In addition, the longitudinal slot in which the radiation source is movably positioned is as long as possible and extends advantageously over the entire length of the measuring cell. This has the further advantage that it simplifies the diffusion of the gas mixture to be analyzed. The rapid gas exchange, i.e., the good passage of air through the longitudinal slot, results in a short $T_{go}$ time. Faster mass exchange is achieved. It is not necessary to install a pump. The response time is reduced.

The cell advantageously takes the form of a metal tube made, for example of aluminium or stainless steel, which may possess a diffusely reflecting inner surface to improve its optical characteristics.

It is particularly advantageous to arrange an interference filter between the radiation source and the detector. Depending on the pass-band range of this filter, the gas analyzer according to the present invention can be adapted to any gas needing to be analyzed which absorbs in the wavelength range of the radiation emitted by the radiation source.

The gas analyzer is advantageously located in a housing which is at least partially gas-permeable, and which may be provided on one side with an opening which is covered, for example, with non-woven metal fibre material. This creates a large inlet zone for the gas to be measured and offers the advantage of improved diffusion and convection properties. The rapid mass exchange between the gas space and the cell also results in short response times by the gas analyzer when gas impinges on it. The mass exchange through diffusion may also be overlain by convective mass exchange caused by heating in the area of the radiation source.

The good retention properties of the non-woven metal fibre material with regard to particles, suspended matter and precipitable contaminants means that the optical elements of the measuring system tend to become less fouled by dirt build-up. It is also possible to use the gas analyzer according to the present invention even in severe operating conditions, e.g. when measuring gas flows carrying a particle load. In addition, the non-woven metal fibre material acts as a flow rectifier and minimizes the possibility of the measurement signal being dependent on aerodynamic flow conditions in the gas space. The non-woven metal fibre material can be cleaned by reverse flushing.

It is advantageous that the optical components of the gas analyzer according to the present invention are in good thermal contact with each other. This reduces the risk of the optical system becoming maladjusted due to thermal influences and thereby causing measurement errors.

The subject of the present invention is also an improved cell for measuring the concentration of a gas in a gas mixture. The cell has the form of a long tube which has a slot running its entire length. The measuring cell consists preferentially of metal, such as stainless steel, and it posses preferably a non-specular reflecting inner surface in order to permit diffuse reflection of the beam inside the cell. The underside of the measuring cell according to the present invention possesses advantageously one or more boreholes by means of which it can be fixed in a housing.

BRIEF DESCRIPTION OF THE DRAWINGS

An embodiment of the present invention is described in more detail below on the bases of the attached drawings, which show.

DETAILED DESCRIPTION OF THE PREFERRED EMBODIMENTS

Figure 1:
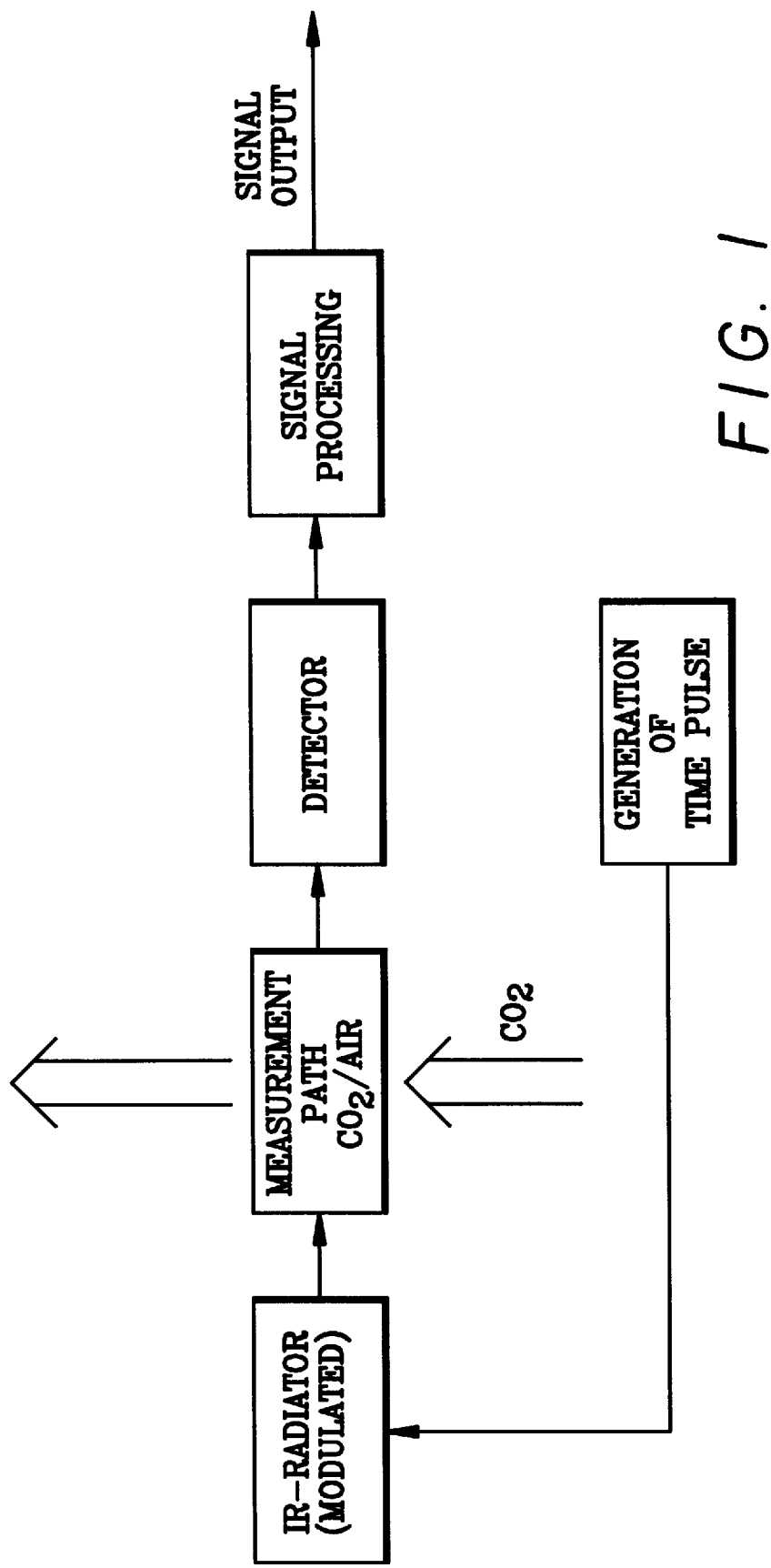
FIG. 1 illustrates in block diagram form a general sketch showing the elements in the circuitry of the gas analyzer according to the present invention.

The general sketch of the system elements shown in FIG. 1 relates to an NDIR single-beam photometer using microprocessor technology. A $CO_2$ sensor has been selected as a typical embodiment of the present invention. $CO_2$ possesses an absorption maximum at a wavelength of 4.24 $\mu$m. Therefore, the radiation source required is an infrared radiation source, e.g. in the form of a long-lived, low-drift, miniaturized IR radiator. In the simplest and preferred case, this can be a miniature incandescent light bulb. Thin-film or thick-film surface radiators may also be used as the IR radiation source.

The IR radiation source is modulated by means of an oscillator which supplies timing pulses. When a miniature incandescent light bulk is used, the clock frequency is a few Hz; the use of thin-film radiators permits clock frequencies of up to 100 Hz. Since no mechanically moving parts (e.g. a chopper wheel) are used, a miniaturized design is possible.

The electromagnetic radiation emitted by the radiation source travels along the measuring path containing the gas to be measured and, after passing through an interference filter, it impinges on a detector. The interference filter can be used as a discrete component or it may also be integrated into the detector. The pass-band of the interference filter is adapted to a specific absorption band of the gas component to be measured. In the example, this is the $CO_2$ absorption band at 4.24 $\mu$m. An infrared-sensitive electronic component, e.g. a pyroelectric detector or a thermopile, is used as the detector. Semiconductor components (PbS, PbSe) may also be used. The output signal of the radiation-sensitive detector is detected by a phase-controllable AC gain circuit with tunable recognition of the zero-crossing point.

The clocking of the radiation source, which is necessary for example when a detector is used that responds solely to the radiation intensity, results in a periodically delayed increase and decay of the thermally induced emission, before or after the maximum radiator temperature is reached. Capacitative or comparable electronic coupling procedures permit AC voltage balancing of the modulated detector signal. By triggering the zero-crossing point, the phase switching point for the phase-dependent signal amplification can be determined. During the desired signal phase, a radiator temperature optimized to the absorption of the measured gas can be supplied. Signal components obtained during the thermal decay and heat-up phases can be compensated against the desired signal phase in order to eliminate disruptive signals. The signal output is optionally an electric voltage (0 to 10 V) or a current (0/4 tp 20 mA).

Figure 2A:
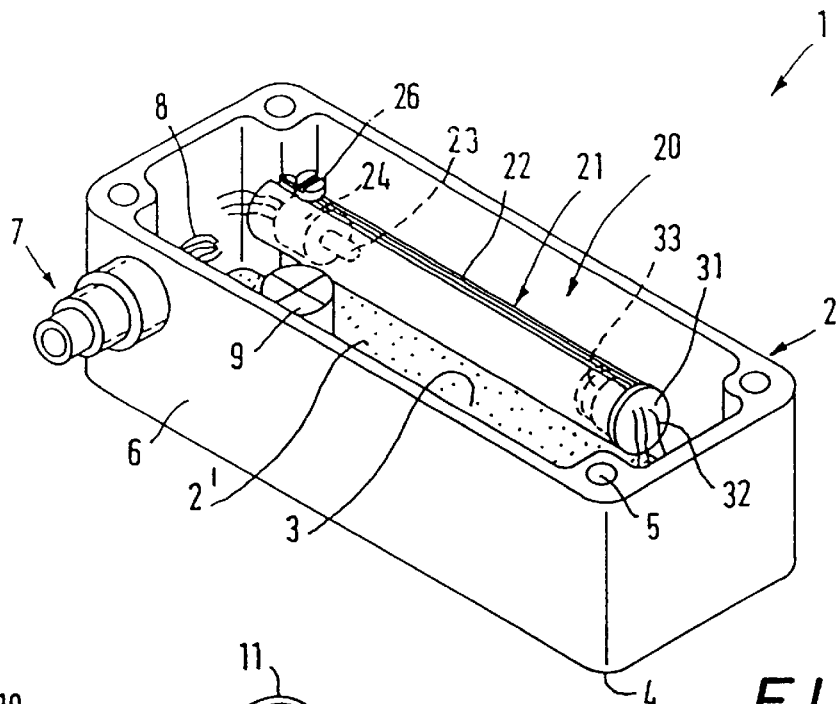
FIG. 2a is a perspective, partially diagrammatic view of the gas analyzer according to the present invention positioned in a housing.

Together with an integrated temperature sensor circuit it is possible to generate a temperature-compensated signal. Another possibility is to use a temperature-dependent radiation source. FIG. 2a illustrates one possible embodiment of the gas analyzer 20 according to the present invention. The housing 2 holds the electronic components; here, only a circuit board 3 is indicated at the bottom of the housing 2. Threaded holes 5 are provided in the corners 4 of the housing 2. One side wall 6 of the housing 2 carries the signal port 7 which is connected via a cable 8 with the circuits on the board 3 and is also used to supply power. Reference number 9 indicates an electrolytic capacitor, 200 $\mu$F.

Figure 2B:
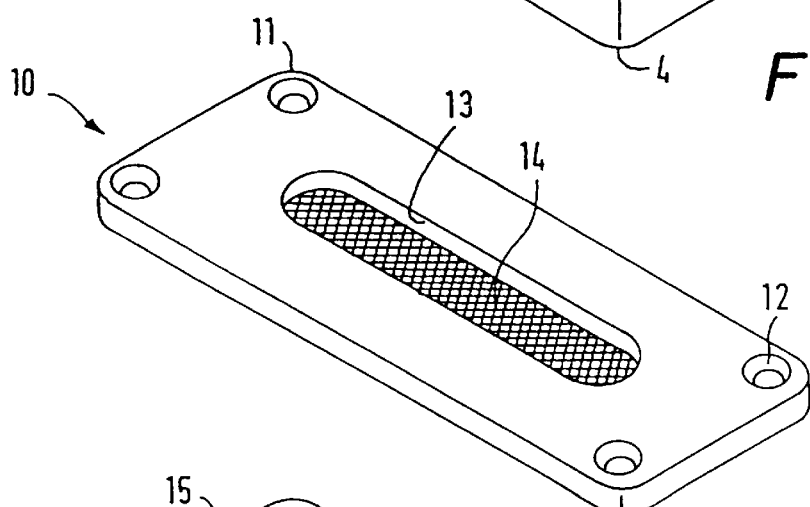
FIGS. 2b, 2c show the cover of the housing shown in FIG. 2a, seen from above and below.
Figure 2C:
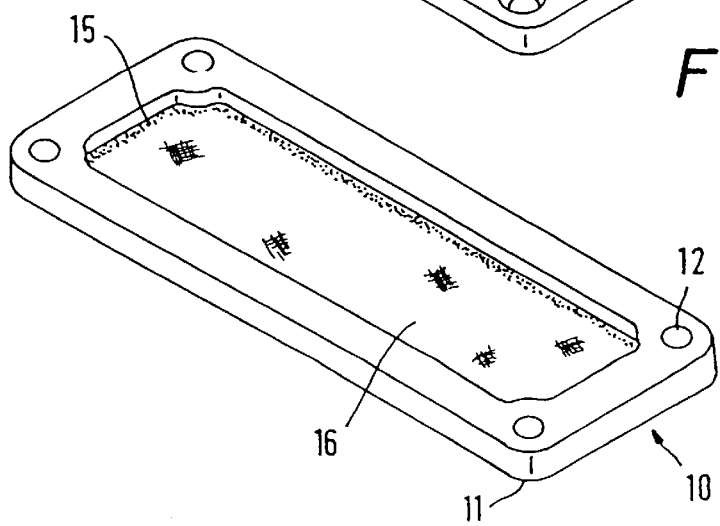

FIGS. 2b and 2c show a cover 10 for closing the housing 2. At its four corners 11, the cover is provided with boreholes 12. When the cover 10 is placed on the housing 2, the holes 5 and 12 line up and the cover is bolted into place.

The cover 10 also possesses an opening 13 which serves as an inlet for the gas. On the side facing the external atmosphere, this opening is covered over by metal mesh 14. On the side facing towards the measuring cell, as can be seen in FIG. 2c, a non-woven metal fibre fabric 16 is attached, e.g. bonded with adhesive 15, to the metal mesh 14 or to the inner surface of the cover 10. The non-woven metal fibre fabric 16 is made up preferably of fibres up to 2 $\mu$m in diameter which are arranged in tangled mats of fibre of uniform weight per unit area and then compressed to defined thicknesses. Appropriate non-woven metal fibre fabrics possess porosities of up to 80% with at the same time a very narrow pore size distribution. Thus, a large inlet zone is created for the gas to be measured and this offers the advantage of improved diffusion and convection and a reduced tendency for soil build-up to occur. This increases the service life of the gas analyzer.

Figure 3:
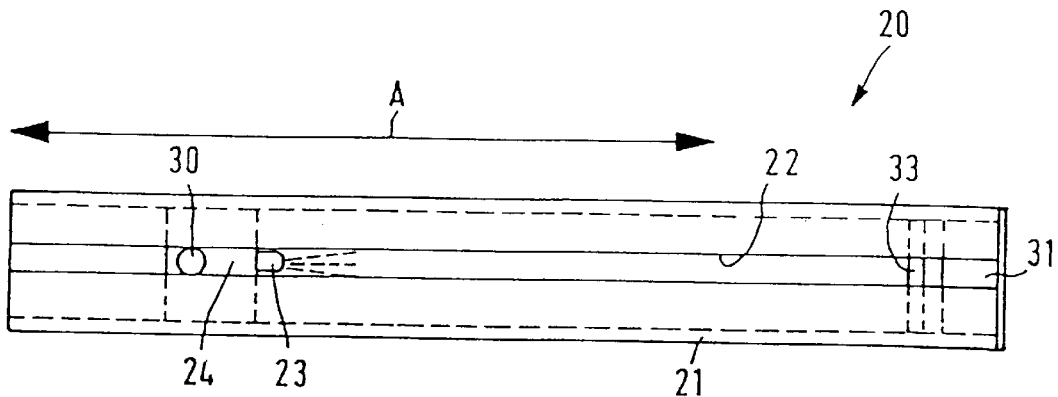
FIG. 3 is a top view of a measuring cell according to the present invention.
Figure 4:
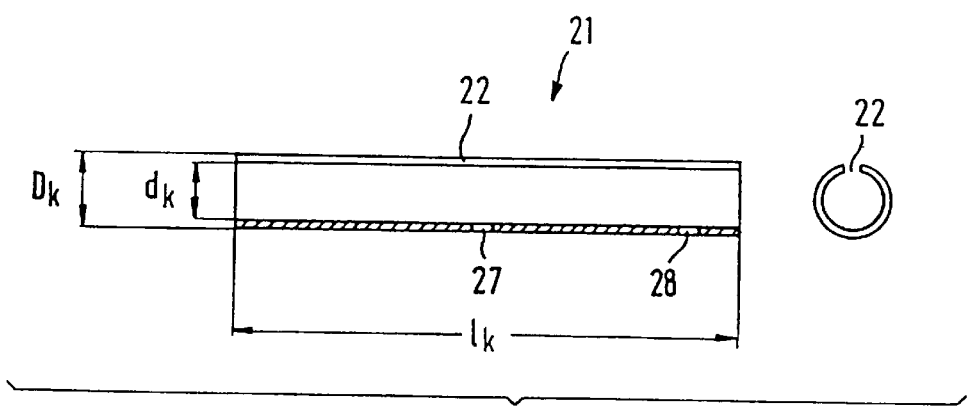
FIG. 4 is a cutaway section of the measuring cell shown in FIG. 3.

It can be seen from FIGS. 2 and 3 that the measuring cell 21 of the gas analyzer 20 according to the present invention comprises a long tube with a longitudinal slot 22, which is not drawn true to scale in FIG. 3 but is made to appear a little longer than it really is. The gas to be measured can be rapidly supplied and removed by diffusion and convection processes through the longitudinal slot 22 which is oriented towards the gas inlet 21. In the present case, the radiation source 23 is a miniature incandescent bulb, which is mounted in a holder 24 and surrounded by a reflector 25. FIG. 4 once again shows in detail for the embodiment described here that the measuring cell 21 has an outer diameter $D_k$ of 10 mm and an inner diameter $d_k$ of 8 mm and a length $l_k$ of approximately 70 mm. The longitudinal slot 22 is about 2 mm wide. On the underside of the measuring cell 21, opposite the longitudinal slot 22, are arranged two boreholes 27, 28 fitted with an M3 thread; borehole 27 is arranged about 7.5 mm from the rear end 7' of the measuring cell 2, and borehole 28 is arranged about 37 mm from that end. The material is V4A stainless steel.

Ideally, the measuring cell 21 with the longitudinal slot 22 is positioned directly behind the metal mesh 14, and fits tightly against it. Then, the gas volume to be flushed is fairly exactly the (low) volume of the measuring cell, so that short response times can be achieved. The space for the measured gas in this case is then actually the entire geometrical space above the metal wire mesh (e.g. an office, auditorium). The number 2' denotes a dead space in the housing which, however, has to be flushed out. This dead space 2' should be kept small.

Figure 5:
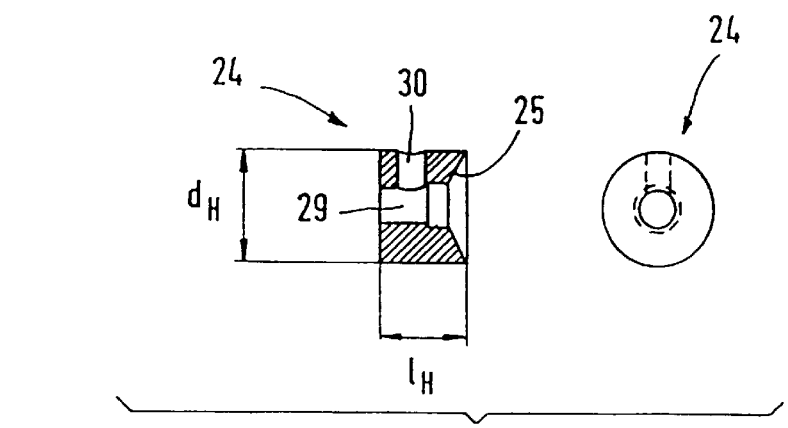
FIG. 5 is a cross section through a holder for a radiation source.

In FIG. 5, the holder 24 for the radiation source 23 is once more shown. It has a diameter $d_H$ of about 8 mm which corresponds to the inner diameter $d_k$ of the measuring cell 21, and it has a length $l_H$ of 6 mm. A conically enlarged through hole 29 accepts the radiation source 23. The conical enlargement is designed as a reflector 25 which surrounds the radiation source 23. At right angles to the through hole 29, the holder 24 is provided with a borehole 30 having an M2 thread for the clamping screw 26. The holder 24 is inserted into the measuring cell 21 with the borehole 30 being oriented towards the longitudinal slot 22. Then the clamping screw 26 is screwed into the borehole 28. The head of the clamping screw is wider than the longitudinal slot 22 so that, when the screw 26 is screwed into the borehole 30 a clamping effect is achieved between the screw 26 and the measuring cell 21. In this way, the holder 24 with the IR radiation source 23 can be moved in the direction of the arrow A in FIG. 3, in the longitudinal slot of the measuring cell, which slot is open to the gas to be measured.

FIG. 3 also shows a detector 31 which is mounted in the measuring cell at the opposite end 21' from the radiation source 23. The detector 31 is connected by wires 32 with the circuitry on the board 3. The detector 31 possesses the largest possible detector surface which, in the embodiment illustrated, corresponds approximately to its cross sectional area. Ahead of the detector is additionally mounted an interference filter 33. But the interference filter may also be integrated into the detector. In the embodiment illustrated, the filter is transparent to IR radiation in the 4.24 $\mu$m wavelength range. The length of the measurement pathway, i.e. the distance between the radiation source 23 and the detector 31 is variable and can be optimized for different gas concentration ranges.

In this particular embodiment, the individual components constituting the optics of the sensor are in good thermal contact with one another. In conjunction with the fact that the radiation source 23 can be guided along the measurement pathway, given also the diffuse reflection on the inner wall of the measuring cell and the use of a detector 31 with a large detector surface, this means that any thermally induced maladjustments of the optical system, and any measurement errors resulting therefrom, are negligibly small. This offers advantages over gas sensors with complicated imaging optics when mirrors are used that require precise adjustments and isothermal operation of mechanical systems.

What is claimed is:

1. A gas analyzer for continuously determining the concentration of a gas in a gas mixture, comprising:

a measuring cell including a longitudinal slot;

a radiation source and a detector operatively associated with said measuring cell, said radiation source being slidingly arranged in said slot; and signal processing means connected to said measuring cell and said detector.

2. The gas analyzer as defined in claim 1, further comprising:

a clamping screw for fixing said radiation source to said measuring cell.

3. The gas analyzer as defined in claim 2, wherein said radiation source includes a holder having a borehole for said clamping screw.

4. The gas analyzer as defined in claim 3, wherein said holder includes a reflector.

5. The gas analyzer as defined in claim 1, wherein said detector and said radiation source are mounted at opposed ends of said measuring cell.

6. The gas analyzer as defined in claim 1, wherein said detector has a detector surface which is equal in size to its cross sectional area.

7. The gas analyzer as defined in claim 1, wherein said measuring cell has the form of a tube, made of one of aluminum and stainless steel.

8. The gas analyzer as defined in claim 1, wherein said longitudinal slot extends over the entire length of said measuring cell.

9. The gas analyzer as defined in claim 1, wherein said measuring cell has a diffusely reflecting inner surface.

10. The gas analyzer as defined in claim 1, further comprising:

an interference filter arranged between said radiation source and said detector, said interference filter having a pass band that is matched to the absorption maximum of a specific absorption band of the gas component to be determined.

11. The gas analyzer as defined in claim 10, wherein said interference filter is integrated into said detector.

12. The gas analyzer as defined in claim 10, further comprising:

an at least partially gas-permeable housing within which said measuring cell is mounted.

13. The gas analyzer as defined in claim 12, further comprising:

a non-woven metal fibre fabric, wherein said housing includes an opening covered by said non-woven metal fibre fabric.

14. The gas analyzer as defined in claim 13, wherein said measuring cell and said radiation source are arranged in said housing in such a manner that they are in good thermal contact with one another.

15. The gas analyzer as defined in claim 12, wherein said measuring cell and said radiation source are arranged in said housing in such a manner that they are in good thermal contact with one another.

16. A measuring cell for photometrically measuring the concentration of a gas in a gas mixture in a gas analyzer, the gas analyzer including said measuring cell, a radiation source and a detector operatively associated with said measuring cell, and signal procesing means connected to said measuring cell and the detector, said measuring cell comprising a tube having a longitudinal slot running over its entire length, for slidably arranging the radiation source therein.

17. The measuring cell as defined in claim 16, wherein said tube is made of metal.

18. The measuring cell as defined in claim 17, wherein said metal is one of aluminum and stainless steel.

19. The measuring cell as defined in claim 16, wherein said tube has a diffusely reflecting inner surface.

20. The measuring cell as defined in claim 16, wherein said tube includes at least one borehole opposite said slot for fixing said tube to a housing.

* * * * *